United States Patent
Sookdeo et al.

(10) Patent No.: US 10,617,264 B1
(45) Date of Patent: Apr. 14, 2020

(54) FOOT SANITIZING DEVICE

(71) Applicants: Arthur N. Sookdeo, Coral Springs, FL (US); Jared A. Maharajh-Sookdeo, Coral Springs, FL (US)

(72) Inventors: Arthur N. Sookdeo, Coral Springs, FL (US); Jared A. Maharajh-Sookdeo, Coral Springs, FL (US)

( * ) Notice: Subject to any disclaimer, the term of this patent is extended or adjusted under 35 U.S.C. 154(b) by 0 days.

(21) Appl. No.: 15/876,333

(22) Filed: Jan. 22, 2018

Related U.S. Application Data (63) Continuation-in-part of application No. 15/432,727, filed on Feb. 14, 2017, now abandoned.

(51) Int. Cl.
| | |
|---|---|
| *A47K 7/02* | (2006.01) |
| *A47K 7/04* | (2006.01) |
| *A46B 11/00* | (2006.01) |
| *A61H 7/00* | (2006.01) |

(52) U.S. Cl.
CPC ............ *A47K 7/026* (2013.01); *A46B 11/002* (2013.01); *A47K 7/04* (2013.01); *A61H 7/002* (2013.01); *A46B 2200/1006* (2013.01); *A61H 2201/164* (2013.01); *A61H 2205/12* (2013.01)

(58) Field of Classification Search
CPC .............. A47K 7/02; A47K 7/04; A47L 23/00
See application file for complete search history.

(56) References Cited

U.S. PATENT DOCUMENTS

| | | | | |
|---|---|---|---|---|
| 4,532,668 A * | 8/1985 | Slonicki | ................ | A47K 7/026 15/104.92 |
| 5,163,200 A * | 11/1992 | Carlin | .................... | A47K 7/026 15/104.92 |
| 5,520,618 A * | 5/1996 | Massiet | ................ | A46B 11/063 132/74.5 |
| 6,223,379 B1 * | 5/2001 | Martin | ................... | A47K 3/022 15/104.92 |
| 6,568,000 B1 * | 5/2003 | Kaufman | ............... | A47K 3/022 4/541.5 |
| 6,684,444 B2 * | 2/2004 | Wheeler | ................ | A47K 7/026 15/110 |
| 7,266,857 B1 * | 9/2007 | Mezyed | ................. | A47K 7/026 15/104.92 |
| 8,763,191 B1 * | 7/2014 | Milligan | ................. | A47L 23/02 15/104.92 |
| 9,609,984 B1 * | 4/2017 | Kelly | ........................ | A47K 7/04 |
| 2002/0152566 A1 * | 10/2002 | Nappi, Sr. | ............... | A47L 23/02 15/36 |
| 2002/0189039 A1 * | 12/2002 | Schlem | ................... | A47L 23/02 15/104.92 |

(Continued)

*Primary Examiner* — Michael D Jennings
(74) *Attorney, Agent, or Firm* — John Rizvi; John Rizvi, P.A.

(57) ABSTRACT

A foot sanitizing device is provided including at least one foot sanitizing unit having a base and a one foot cavity formed on a top side of the base. A fluid reservoir may be provided on the base and may comprise a reservoir interior in fluid communication with the foot cavity and configured to contain a supply of sanitizing fluid. A user-operable pump may be provided on the fluid reservoir and configured to pump the sanitizing fluid from the fluid reservoir into the at least one foot cavity. At least one foot insert is removably attachable to the foot cavity to provide a contact interface for a user's foot to rest on. The user can place the foot on the foot insert and apply sanitizing fluid onto the foot by operating the pump.

14 Claims, 8 Drawing Sheets

(56) References Cited

U.S. PATENT DOCUMENTS

2007/0143918 A1* 6/2007 Cafaro .................. A47K 3/022
          4/622
2008/0104782 A1* 5/2008 Hughes .................. A47L 23/02
          15/30
2017/0071824 A1* 3/2017 Park ...................... A61H 39/04

* cited by examiner

FOOT SANITIZING DEVICE

CROSS-REFERENCE TO RELATED APPLICATIONS

This application is a Continuation-In-Part (CIP) of U.S. Utility patent application Ser. No. 15/432,727, filed on Feb. 14, 2017, which is incorporated by reference herein in its entirety.

FIELD OF THE INVENTION

The present invention relates generally to foot sanitizing devices, and more particularly, to a foot sanitizing device which includes one or more foot-receiving cavities each disposed in fluid communication with a sanitary fluid reservoir typically fitted with a fluid pump to facilitate pumping sanitary fluid from the sanitary fluid reservoir into the foot-receiving cavity or cavities.

BACKGROUND OF THE INVENTION

In many cultures, personal hygiene is important. In the United States, for example, it is not unusual for many active persons to bathe or shower two or more times each day. Hand washing is frequently performed regularly before meals. Antimicrobial hand sanitizing gels are commonly used to sanitize the hands of a user. There are numerous circumstances in which it may be desirable for a user to sanitize his or her hands. For example, many persons prefer to sanitize their hands before eating. Medical personnel may be required to sanitize their hands prior to implementing a medical procedure. Food service personnel may be required to sanitize their hands before handling food in an eating establishment.

Throughout day-to-day activities, the feet of a person are typically enclosed in shoes or other footwear. Shoes and other footwear serve to maintain the cleanliness of a wearer or user's feet as well as to protect the feet of the user from injury due to objects on the ground and from objects which may inadvertently fall on the user's feet. However, enclosure of the user's feet in footwear may cause the feet to sweat and develop a disagreeable smell to others, particularly if the footwear is removed from the feet. Moreover, in some religious traditions, foot washing may be desirable for ritual cleanliness. Therefore, various types of foot sanitizers have been devised for the purpose of sanitizing the feet of a user. However, conventional foot sanitizers have had various drawbacks, such as complexity of design and/or use.

Accordingly, there is an established need for a foot sanitizing device which allows a user to sanitize their feet in a simple, quick, convenient and yet effective manner. Preferably, the sanitizing device should be able to be manufactured cost effectively such that the device can be provided to users at reasonable cost. Also preferably, the device should be durable.

SUMMARY OF THE INVENTION

The present invention is generally directed to a foot sanitizing device which includes one or more foot-receiving cavities each disposed in fluid communication with a sanitary fluid reservoir which may be fitted with a fluid pump to facilitate pumping sanitary fluid from the sanitary fluid reservoir into the foot-receiving cavity or cavities. The pump can be easily and conveniently operated by a user's hand or foot prior to or while placing a foot within the foot-receiving cavity. The foot sanitizing device can be made of washable materials such as, but not limited to, silicone and plastic.

In a first implementation of the invention, a foot sanitizing device comprises at least one foot sanitizing unit, each foot sanitizing unit comprising a base, a fluid reservoir and a user-operable pump. The base has a foot cavity formed on a top side of the base. The fluid reservoir is provided on the base and comprises a reservoir interior which is in fluid communication with the foot cavity and is configured to contain a supply of fluid. In turn, the user-operable pump is configured to pump fluid from the fluid reservoir into the foot cavity. The foot sanitizing device further includes a set of one of more foot inserts. Each foot insert is removably attachable to the foot cavity to provide a contact interface for a user's foot to contact.

In a second aspect, the base of each foot sanitizing unit and the foot cavity can be elongated along a common longitudinal direction.

In another aspect, each foot sanitizing unit can further include a pair of base side walls extending upwardly from opposite transverse side edges of the base.

In another aspect the base can further include at least one bottom suction cup extending downwardly from the base and configured to facilitate securement of the base on a hard floor or surface.

In another aspect, the base can further include at least one bottom spike extending downwardly from the base and configured to facilitate securement of the base on a carpet.

In yet another aspect, the at least one foot sanitizing unit can include two or more foot sanitizing units, wherein each foot sanitizing unit comprises at least one first fastener portion on one side of the base and at least one second fastener portion on an opposite side of the base. Each first fastener portion is configured to interlock with a corresponding one of the at least one second fastener portion.

In another aspect, the at least one first fastener portion can be arranged on one of the pair of base side walls and the at least one second fastener portion can be arranged on the other of the pair of base side walls.

In another aspect, the first fastener portion can include an interlock flange and the second fastener portion can include an interlock cavity configured to couple to the interlock flange.

In yet another aspect, the fluid reservoir can be arranged at a proximal longitudinal end of the base and the foot cavity can be arranged distally of the fluid reservoir and pump.

In another aspect, each foot sanitizing unit can include a fluid conduit extending from the fluid reservoir to a fluid discharge opening formed in a floor of the foot cavity.

In another aspect, a fluid conduit space can extend along the base and can be configured to receive the fluid conduit.

In another aspect, the fluid conduit can be received in the fluid conduit space such that the fluid conduit does not protrude outwardly from the fluid conduit space.

In yet another aspect, the pump can include an upwardly-directed, elastically-deformable protrusion which is configured to be pressed downward by a user's hand or foot to reduce the size of the reservoir interior and increase pressure within the reservoir interior to force fluid from the reservoir interior towards the foot cavity.

In another aspect, the upwardly-directed, deformable protrusion can be dome-shaped.

In another aspect, the upwardly-directed, deformable protrusion can be elongated in a transverse direction which is perpendicular to a longitudinal direction of the base and foot cavity.

In another aspect, each foot insert can include a foot insert panel configured to fit into the foot cavity and at least one insert locking clip configured to interlock with a companion clip opening in the base.

In another aspect, each foot insert can include at least one fluid discharge opening through which the sanitizing fluid may be discharged towards a top side of the foot insert.

In yet another aspect, each foot insert can include at least one of a rough texture, a plurality of bristles and a plurality of massaging bumps.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a foot sanitizing device which includes one or more foot-receiving cavities each disposed in fluid communication with a sanitary fluid reservoir which may be fitted with a fluid pump to facilitate pumping sanitary fluid from the sanitary fluid reservoir into the foot-receiving cavity or cavities.

Figure 1:
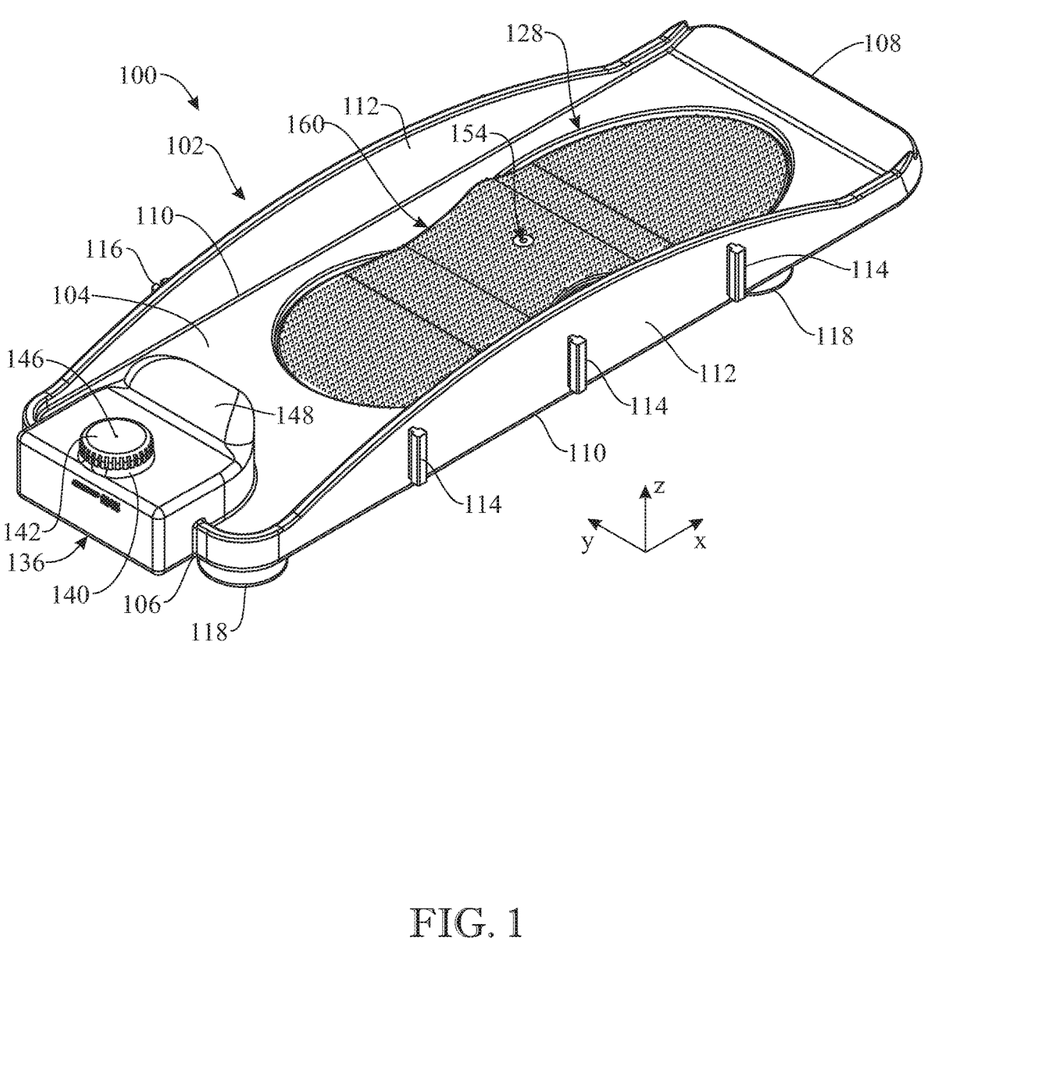
FIG. 1 presents a rear perspective view of a typical foot sanitizing unit of an illustrative embodiment of the foot sanitizing device of the present invention.
Figure 5:
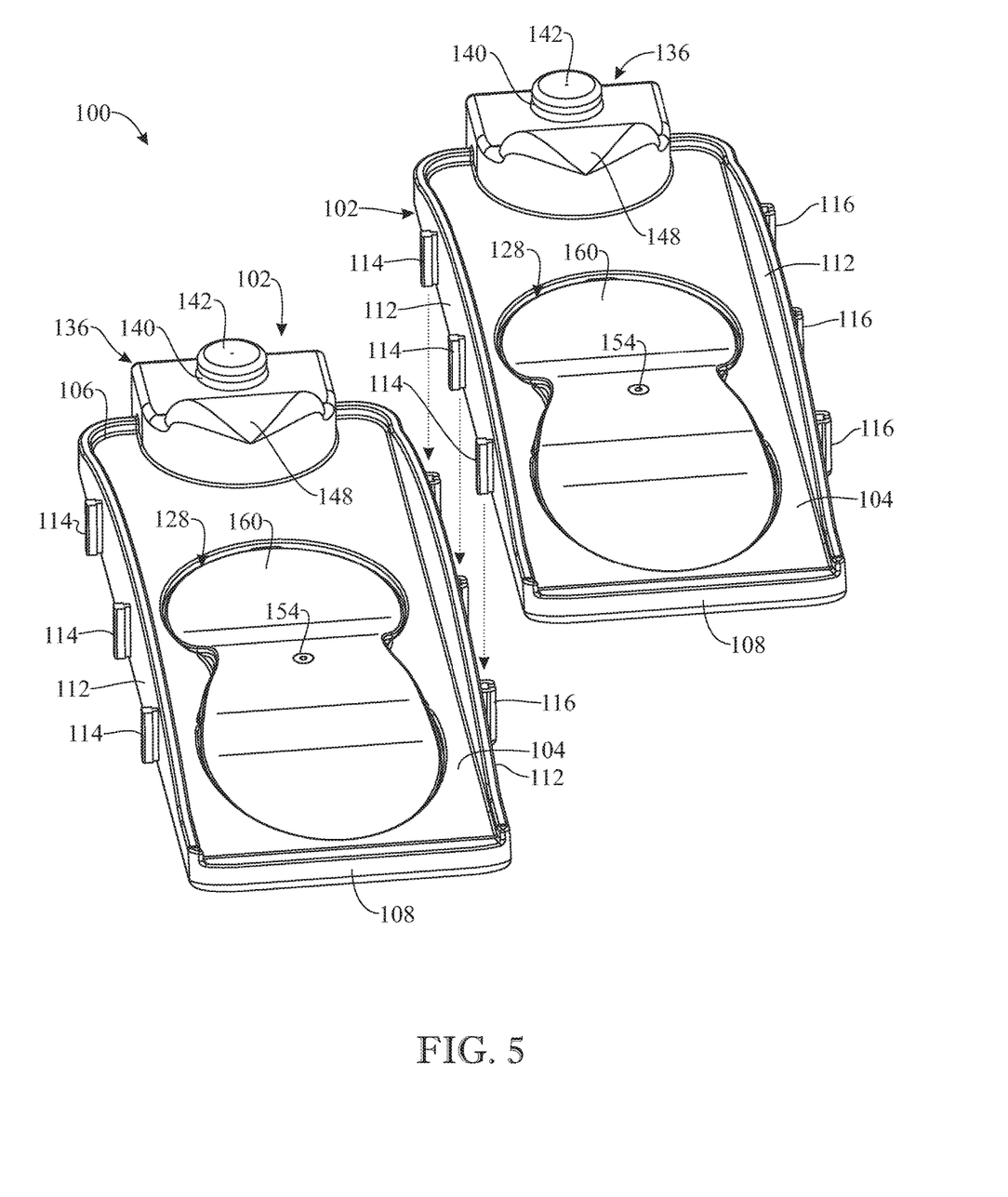
FIG. 5 presents an exploded front perspective view of a pair of foot sanitizing units of the foot sanitizing device of the present invention, more particularly illustrating typical interlocking attachment of the foot sanitizing units according to some applications of the foot sanitizing device of the present invention.
Figure 6:
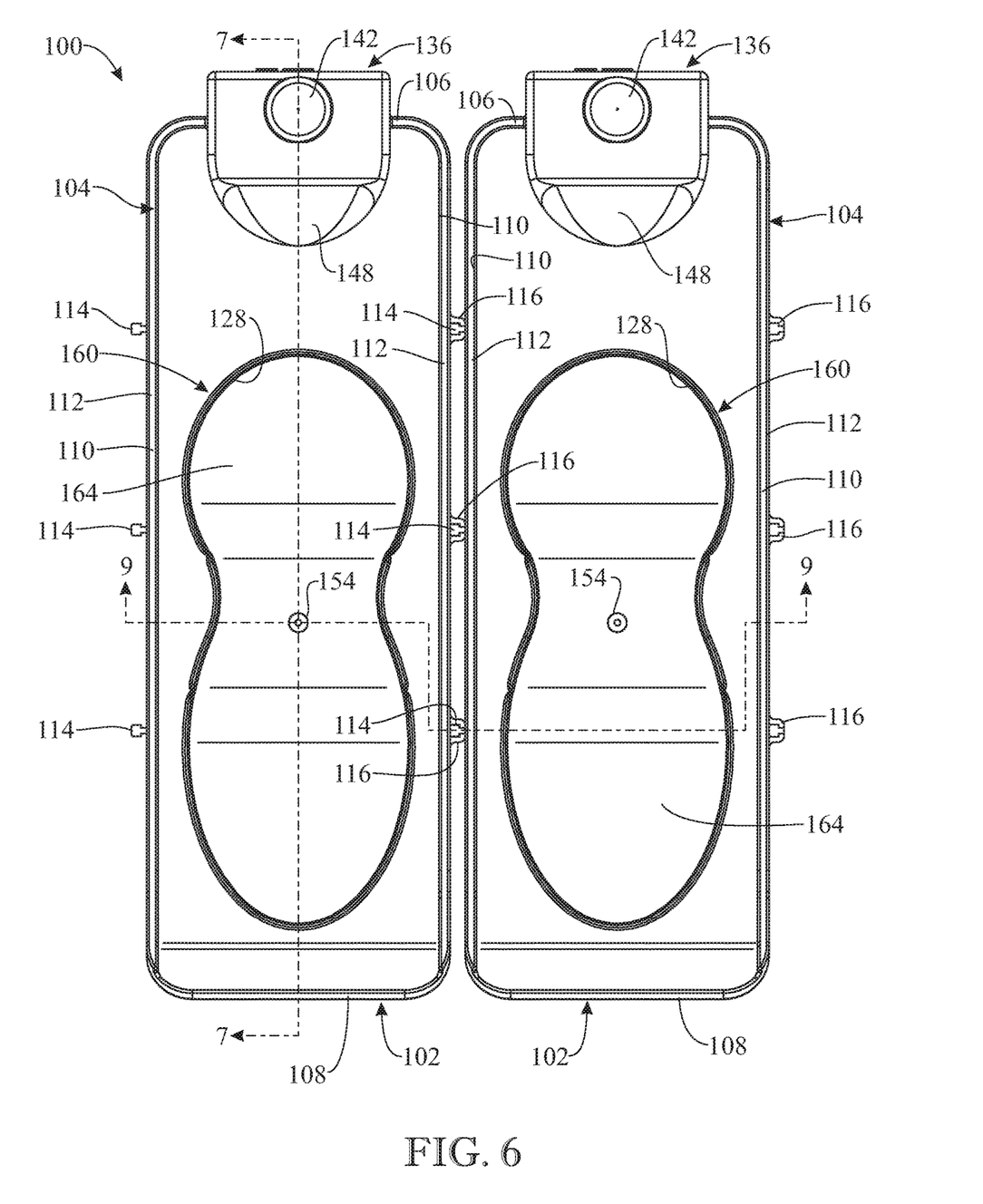
FIG. 6 presents a top view of the interlocking foot sanitizing units of the foot sanitizing device of the present invention illustrated in FIG. 5.

Referring initially to FIG. 1, a foot sanitizing device 100 is illustrated in accordance with an exemplary embodiment of the present invention. As shown, the foot sanitizing device 100 may include at least one foot sanitizing unit 102. In some embodiments, the foot sanitizing device 100 may include a pair of modular foot sanitizing units 102 which may be attached to each other in interlocking relationship, as illustrated in FIGS. 5 and 6 and will be hereinafter described. With continued reference to FIG. 1, each foot sanitizing unit 102 may include a base 104 which may be generally elongated along a longitudinal direction x, which forms an orthogonal three-axis set with a transverse direction y and a vertical direction z, as shown in FIG. 1. The base 104 may have a proximal base edge 106 and a distal base edge 108. A pair of spaced-apart base side edges 110 may extend between the proximal base edge 106 and the distal base edge 108. In some embodiments, a pair of spaced-apart base side walls 112 may extend upwardly from the respective base side edges 110. The base side walls 112 may be rounded as shown, or present alternative shapes. In some embodiments, the base 104 may be fabricated of a soft, flexible and washable material such as, but not limited to, silicone or rubber. The silicone can have a score of 70 on the shore hardness scale, for example and without limitation. In other embodiments, the base 104 may be rigid, such as made of a harder plastic material. In some embodiments, the base 104 may be made of more than one material, such as by having some parts made of silicone and others made of a harder plastic material.

Figure 3:
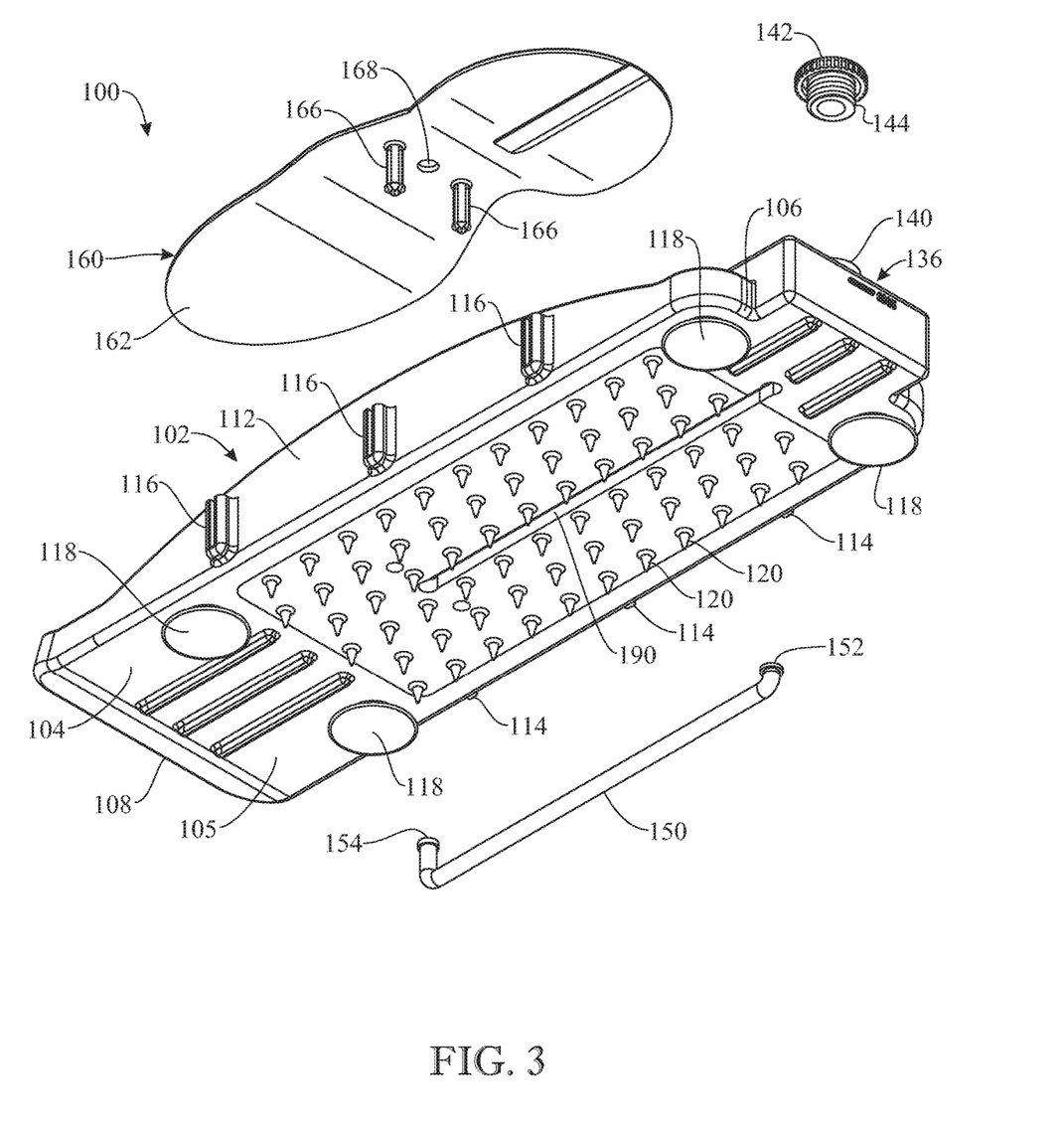
FIG. 3 presents a bottom exploded perspective view of the foot sanitizing unit of the illustrative embodiment of the foot sanitizing device of the present invention.

In some embodiments comprising more than one foot sanitizing unit 102, the foot sanitizing units 102 may be suitably configured to attach to each other in interlocking relationship. Accordingly, as shown in FIG. 1, at least one interlock flange 114 may be provided on one of the base side walls 112 of each foot sanitizing unit 102. As shown in FIG. 3, at least one companion interlock cavity 116 may be provided on the other base side wall 112 of each foot sanitizing unit 102. As illustrated in FIG. 5, the interlock flange or flanges 114 on one foot sanitizing unit 102 may be interlocked with the respective interlock cavity or cavities 116 on another foot sanitizing unit 102 to fasten the foot sanitizing units 102 to each other in adjacent relationship. In some embodiments, as in the present embodiment, the interlock flanges 114 and interlock cavities 116 may be formed in the vertical direction z such that interlocking takes place by inserting the interlock flanges 114 into the interlock cavities 116 and displacing the former vertically with respect to the latter in the vertical direction z. This configuration allows small amounts of fluid contained within at least one foot cavity 128 (which will be described in more detail hereinafter) formed in the base 104 not to be spilled therefrom when connecting or disconnecting the interlock flanges 114 to and from the interlock cavities 116.

Figure 7:
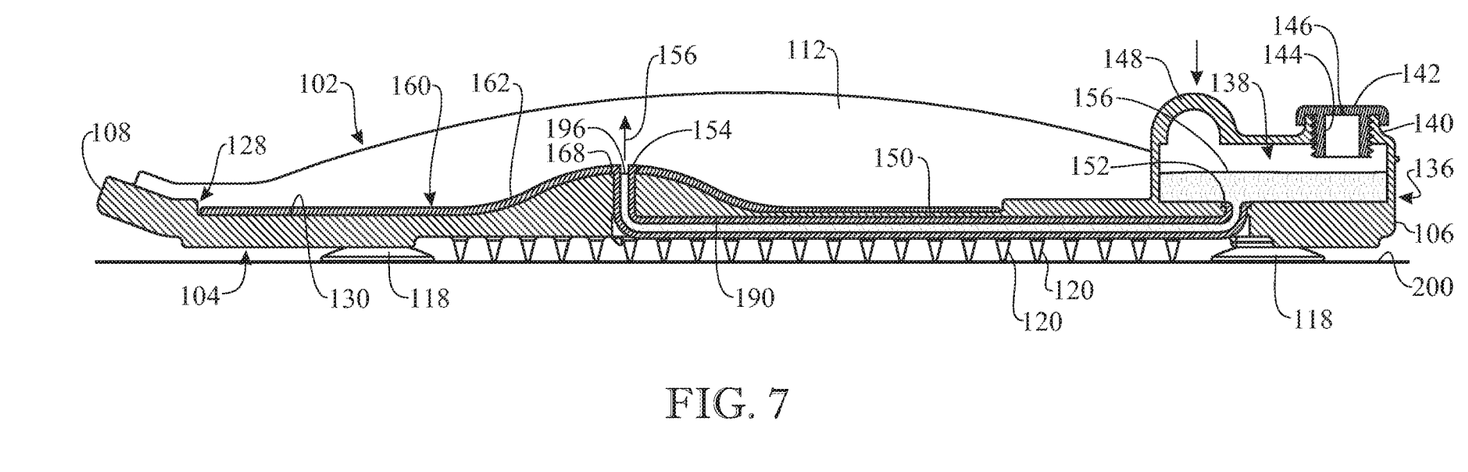
FIG. 7 presents a longitudinal sectional view, taken along section lines 7-7 in FIG. 6, of a foot sanitizing unit of the foot sanitizing device of the present invention, more particularly illustrating typical discharge of sanitizing fluid onto the foot insert.
Figure 8:
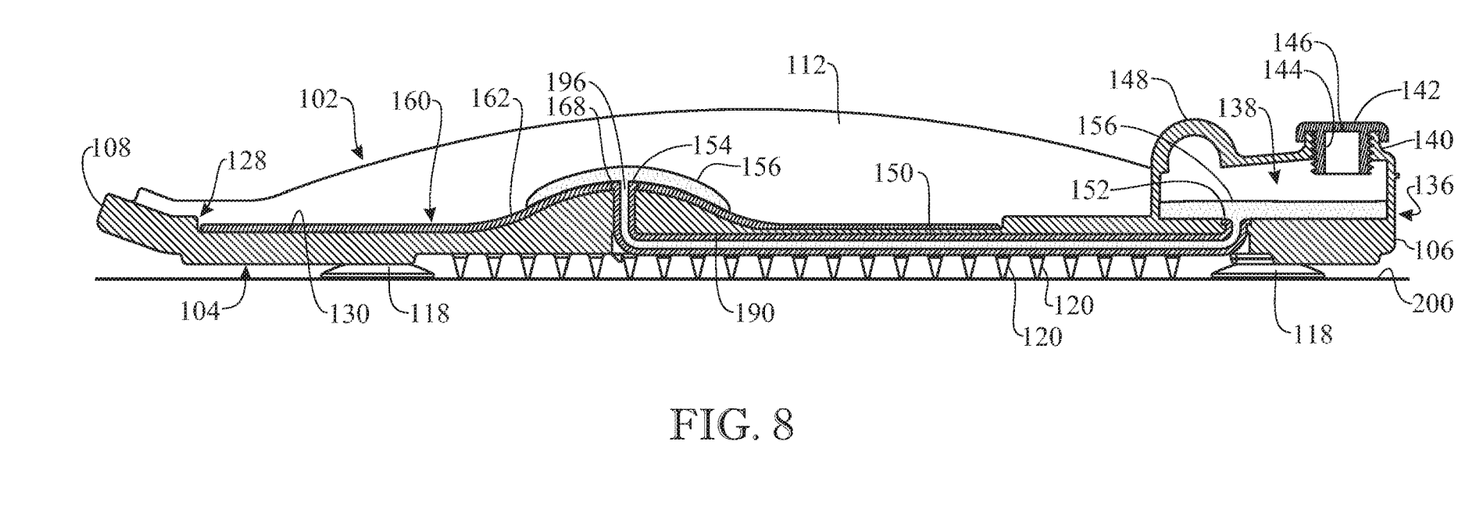
FIG. 8 presents a longitudinal sectional view, taken along section lines 7-7 in FIG. 6, of a foot sanitizing unit of the foot sanitizing device of the present invention, after discharge of sanitizing fluid onto the foot insert.
Figure 9:
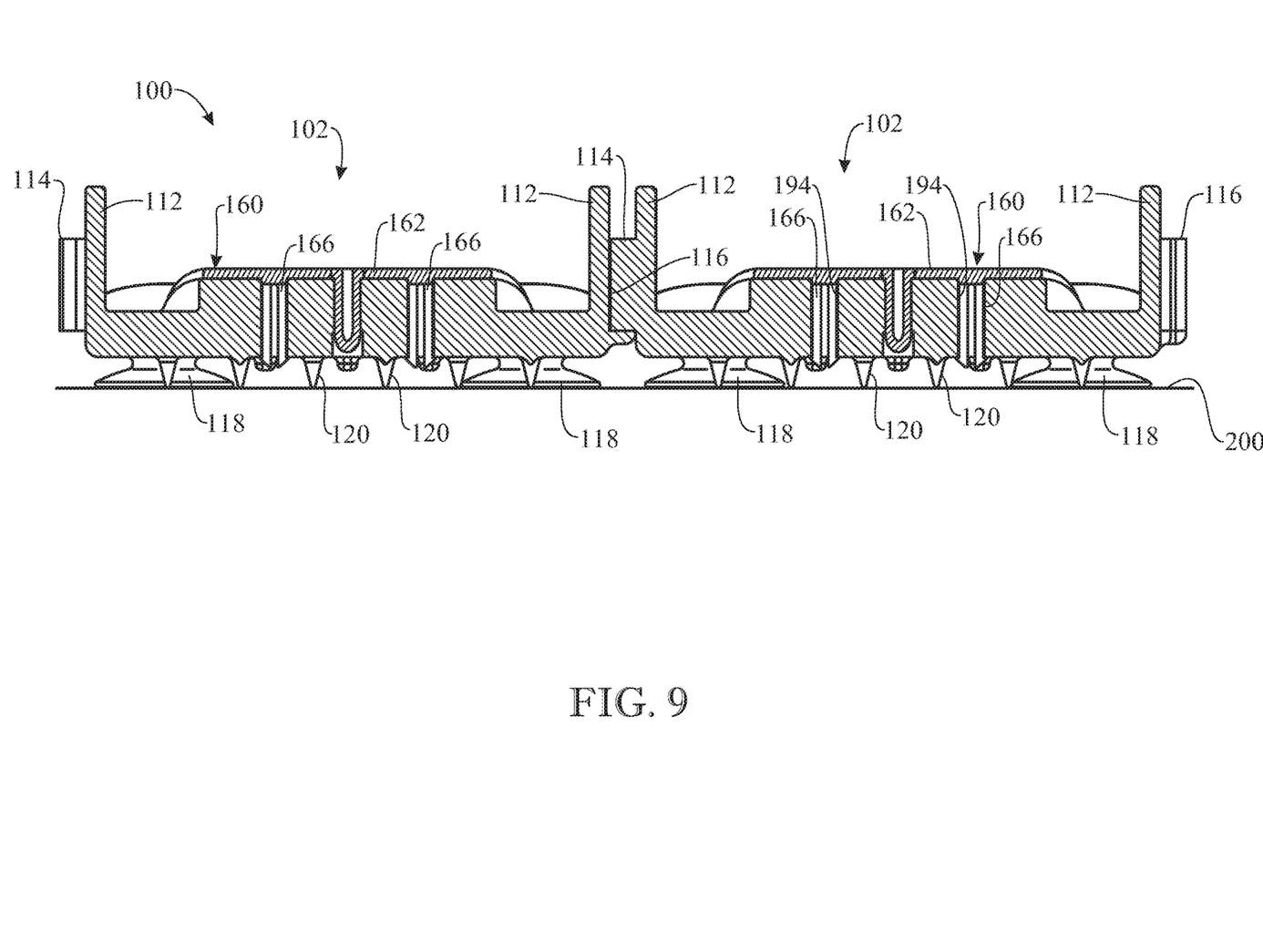
FIG. 9 presents a cross-sectional view, taken along section lines 9-9 in FIG. 6, of the interlocking foot sanitizing units of the foot sanitizing device.

As illustrated in FIG. 3, in some embodiments, at least one suction cup 118 may be provided on the base 104, protruding downwardly from a bottom side 105 of the base 104, to secure the foot sanitizing unit 102 onto a hard, flat floor or other surface 200, as illustrated in FIGS. 7-9. Additionally or alternatively, spikes 120 may be provided on the base 104, protruding downwardly from the bottom side 105 of the base 104, to render the foot sanitizing unit 102 non-slip on a carpeted floor or other surface 200.

Figure 4:
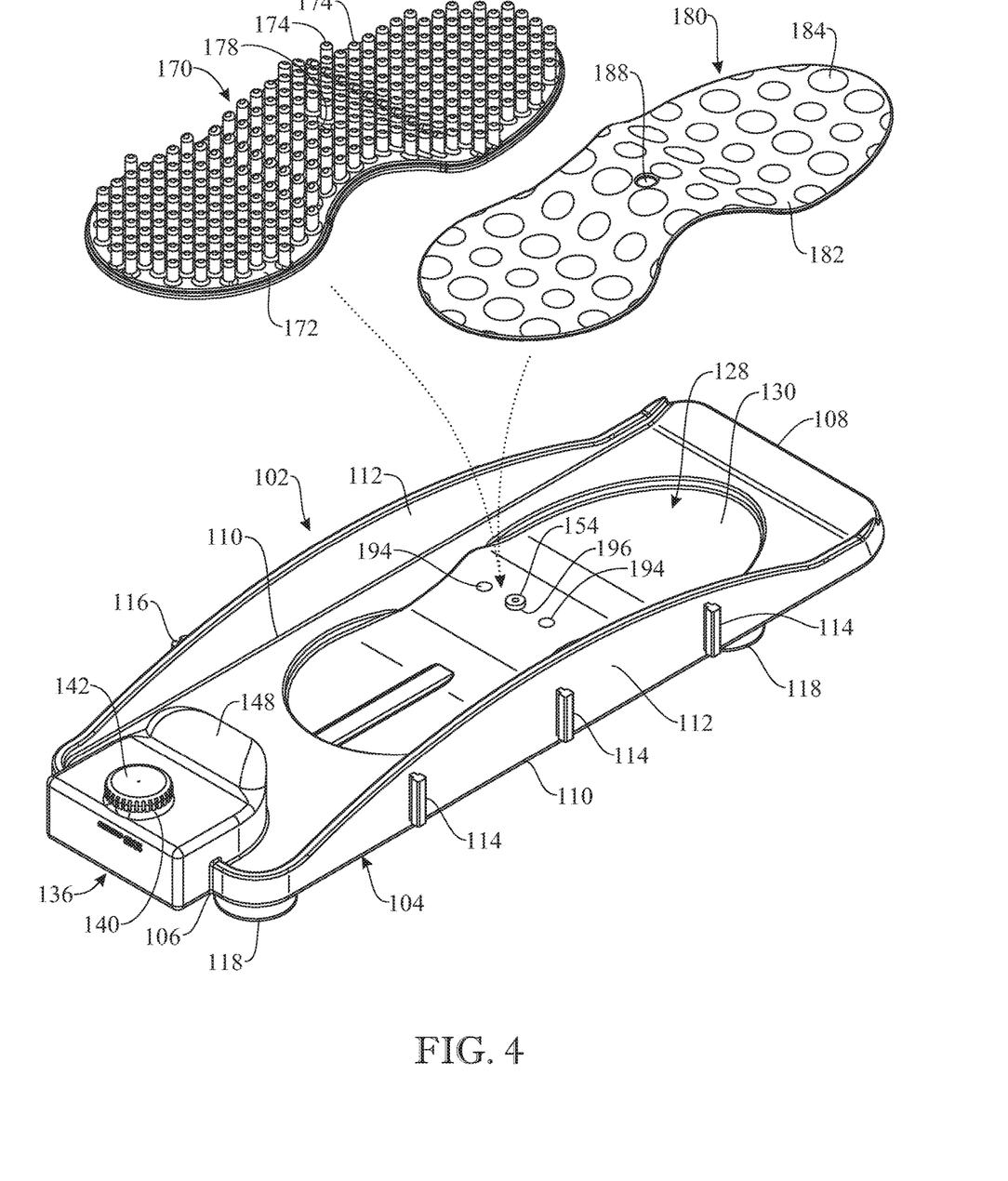
FIG. 4 presents a top exploded perspective view of the foot sanitizing unit of the illustrative embodiment of the foot sanitizing device of the present invention, more particularly illustrating different designs for the foot insert.

As mentioned heretofore, at least one upwardly-oriented foot recess or cavity 128 may be provided in the base 104. The foot cavity 128 may generally approximate the size and shape of a human foot. As illustrated in FIGS. 2 and 4-6, the foot cavity 128 may have a foot cavity floor 130. As illustrated in FIG. 4, at least one clip opening 194 may be provided in the foot cavity floor 130 for purposes which will be hereinafter described. At least one fluid discharge opening 196 may additionally be provided in the foot cavity floor 130 for purposes which will be hereinafter described.

Figure 2:
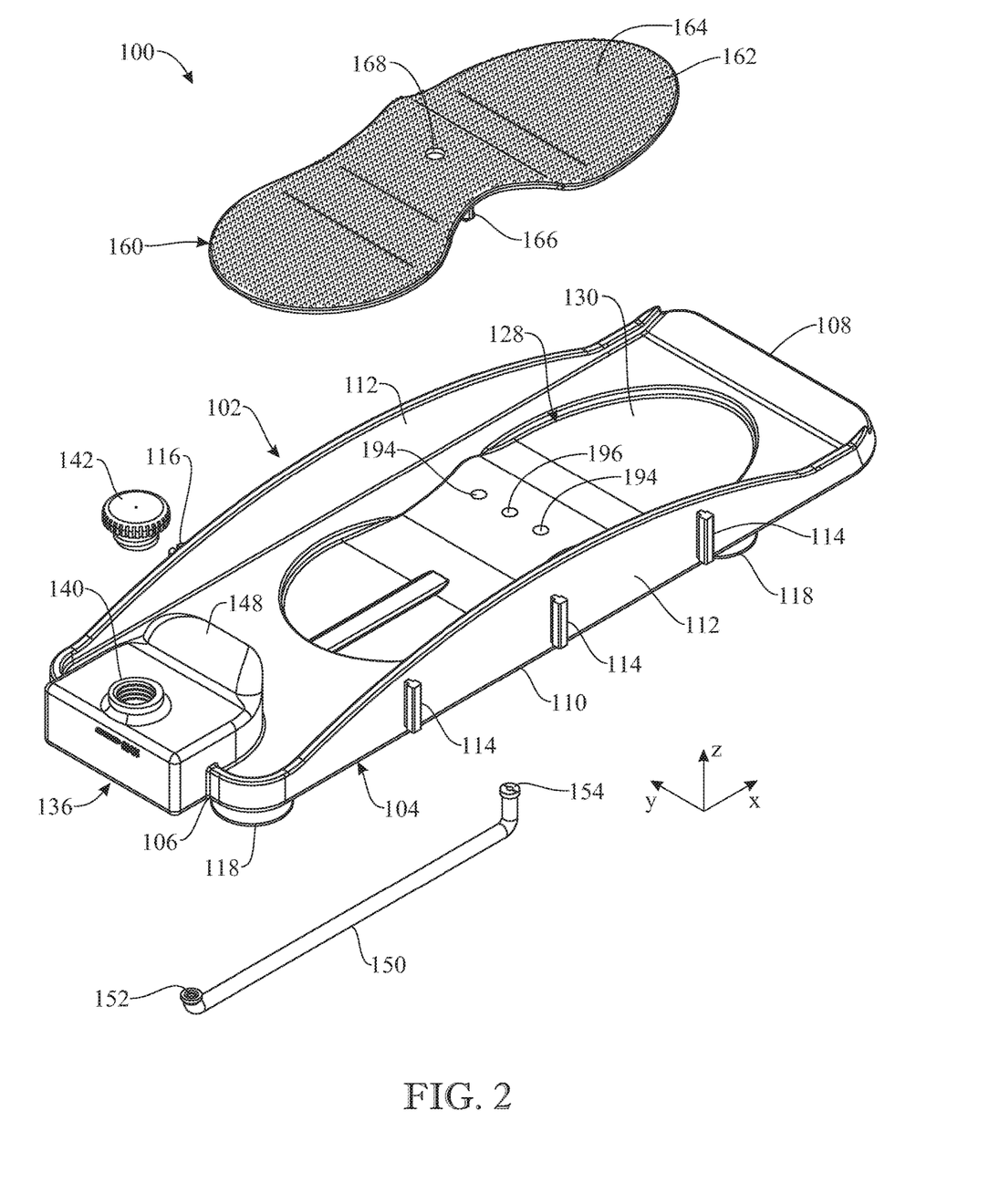
FIG. 2 presents a rear exploded perspective view of the foot sanitizing unit of the illustrative embodiment of the foot sanitizing device of the present invention.

As shown in FIG. 1, a foot insert 160 may be seated in the foot cavity 128. As best shown in the exploded view of FIG. 2, the foot insert 160 may include a foot insert main body or panel 162 which may be fabricated of a flexible sheet material such as rubber or plastic, for example and without limitation. Alternatively, the foot insert 160 may be fabricated of a rigid or semi-rigid material which is shaped to conform to the foot of a user. The foot insert 160 may be secured in place in the foot cavity 128 according to any suitable technique which is known by those skilled in the art. As illustrated in FIGS. 2 and 3, in some embodiments, at least one insert locking clip 166 may extend downward from the foot insert panel 162 of the foot insert 160. Each insert locking clip 166 may be inserted into a corresponding clip opening 194 in the foot cavity floor 130 to secure and stabilize the foot insert 160 in the foot cavity 128. A through opening 168 may be provided in the foot insert panel 162. As best shown in FIGS. 7-9, the opening 168 is configured to align or register with the fluid discharge opening 196 of the foot cavity floor 130 when the foot insert 160 is installed in the foot cavity 128 by connecting the insert locking clips 166 to the clip openings 194.

In some embodiments, the foot sanitizing device 100 may include two or more different and interchangeable foot inserts. For example, the present embodiment includes the aforementioned foot insert 160, shown in FIGS. 1-3, and two additional foot inserts 170 and 180 shown in FIG. 4. Each foot insert 160, 170, 180 can be configured to provide a different sanitizing, therapeutic or sensitive effect on the user's foot. For example, the top side of the foot insert panel 162 of the foot insert 160 shown in FIGS. 1-3 can be provided with a rough, exfoliating finish 164 to promote a deeper cleaning of the skin of the user's foot. In turn, foot insert 170 may include multiple bristles 174 extending upward from the foot insert panel 172, wherein the bristles 174 may function as a foot massager. Foot insert 180 may include a foot insert panel 182 having massaging bumps 184. Though not specifically shown in FIG. 4, foot inserts 170 and 180 are provided with insert locking clips configured to be received and clipped into the clip openings 194, similarly to the insert locking clips 166 of foot insert 160. Accordingly, any one of the plurality of available foot inserts 160, 170 and 180 may be selected by the user for placement in the foot cavity 128 depending on the preferences of the user. As further shown in FIG. 4, the foot inserts 170 and 180 are provided with a respective through opening 178 and 188 serving identical purposes as the through opening 168 of foot insert 160.

Turning once more to FIG. 1, a fluid reservoir 136 may be provided on or integrally formed with the base 104 in fluid communication with the foot cavity 128 typically through the fluid discharge opening 196 formed in the base 104. In some embodiments, the fluid reservoir 136 may be provided at the proximal base edge 106 of the base 104, as illustrated. As shown in FIGS. 7 and 8, the fluid reservoir 136 may have a reservoir interior 138 which is suitably sized and configured to contain a supply of sanitizing fluid 156 or other fluid which is designed to wash, sanitize or otherwise treat the user's foot. A cap 142 may close the reservoir interior 138. The cap 142 is preferably disconnectably and re-connectably attached to the fluid reservoir 136 such that the cap 142 can be repeatedly and reversibly disconnected from and connected to the fluid reservoir 136 to selectively grant or prevent access to the reservoir interior 138. For instance and without limitation, the cap 142 may threadably engage the fluid reservoir 136, such as by having the cap 142 include a male threaded neck 144 configured to thread into a fill neck 140 on the fluid reservoir 136, as shown for instance in FIG. 7. The cap 142 further comprises a small vent 146 for purposes that will be hereinafter described.

A fluid pump 148 may be provided on the fluid reservoir 136. The fluid pump 148 can be operated to pump the sanitizing fluid 156 from the reservoir interior 138 of the fluid reservoir 136 into the foot cavity 128, as will be hereinafter described. In some embodiments, the fluid pump 148 may be formed as an elastically-deformable, upwardly-oriented protrusion which is configured to compress downward when being pressed on by a user with a sufficient force. For instance, the fluid pump 148 can be formed as an elastically-deformable dome-shaped protrusion, as shown. In some embodiments, such as the present embodiment, the fluid pump 148 can be elongated in the transverse direction y, as shown, to facilitate pressing the fluid pump 148 with a user's heel or other part of the foot.

As illustrated in FIGS. 2, 3, 7 and 8, a fluid conduit 150 may establish fluid communication between the reservoir interior 138 of the fluid reservoir 136 and the foot cavity 128. The fluid conduit 150 may be made of a flexible rubber or plastic material, for instance and without limitation, and may have an inlet end 152 at the reservoir interior 138 and an outlet end 154 at the fluid discharge opening 196 of the foot cavity 128. In some embodiments, the fluid conduit 150 may extend through a the through opening 168 in the foot insert 160 to dispense the sanitizing fluid 156 onto the surface of the foot insert 160 upon operation of the fluid pump 148; in alternative embodiments, the outlet end 154 may be adjacent to, and aligned or in registration with, the through opening 168 in the foot insert 160. As illustrated in FIGS. 3, 7 and 8, a fluid conduit recess or space 190 may be molded or otherwise fabricated into the base 104 according to the knowledge of those skilled in the art. The fluid conduit 150 may be received within and extend along the fluid conduit space 190. Preferably, as shown, the fluid conduit 150 does not protrude outwardly from the fluid conduit space 190.

In typical application, a supply of the sanitizing fluid 156 may be placed in the reservoir interior 138 of the fluid reservoir 136. This may be accomplished by removing the cap 142 from the fill neck 140, pouring the sanitizing fluid 156 into the fluid reservoir 136 through the fill neck 140 and reconnecting the cap 142 to the fill neck 140. A user (not illustrated) of the foot sanitizing device 100 may select the type of foot insert among the available foot inserts 160, 170 and 180 for placement in the foot cavity 128. The foot insert 160, 170 or 180 may be secured in place in the foot cavity 128 by inserting the insert locking clips (e.g., insert locking clips 166) into the respective clip openings 194 in the foot cavity floor 130 of the foot cavity 128. As the foot insert 160 is placed in the foot cavity 128, the outlet end 154 on the fluid conduit 150 may align or register with, or extend through, the through opening 168 in the foot insert 160 such that fluid communication is provided between the fluid conduit 150 and the top side of the foot insert 160, 170 or 180.

In some applications, multiple foot sanitizing units 102 may be adjacently secured to each other. Accordingly, the foot sanitizing units 102 may sanitize the respective left and right feet of the user. As illustrated in FIGS. 5, 6 and 9, this may be accomplished by interlocking the interlock flange or flanges 114 on one foot sanitizing unit 102 with the companion interlock cavity or cavities 116 on the adjacent foot sanitizing unit 102.

The user may then place one of his or her bare feet onto each foot insert in the foot sanitizing unit 102. For example, with reference to FIGS. 7-9, the user may have installed the exfoliating foot insert 160, and as such, the user may place his or her foot on said foot insert 160. With his or her other foot, the user may operate the fluid pump 148 (alternatively, the user may operate the fluid pump 148 manually or, prior to placing their foot on the foot insert 160, with the same foot which will be placed on the foot insert 160). When the fluid pump 148 is pressed downward, the size of the reservoir interior 138 decreases, causing the pressure within the reservoir interior 138 to increase. In some embodiments, the vent 146 may allow some air to pass outwardly therethrough (for instance, in case the vent 146 is formed as a through opening extending through the cap 142), in a sufficiently small amount such that pressure is not prevented from increasing within the reservoir interior 138; in other embodiments, the vent 146 may be a one-way valve which allows incoming air and blocks outgoing air from passing through the vent 146). The pressure increase within the reservoir interior 138 forces the sanitizing fluid 156 to be pumped from the reservoir interior 138 of the fluid reservoir 136, through the fluid conduit 150 and discharged onto the surface of the foot insert 160 through the outlet end 154 of the fluid conduit 150. The outwardly-projected sanitizing fluid 156 may contact the bottom and sides of the user's foot, sanitizing the foot. After the first foot of the user is sanitized, the second foot of the user may be sanitized in like manner using the adjacent foot sanitizing unit 102 or the same sanitizing unit 102. It will be appreciated by those skilled in the art that the bristles 174 (FIG. 4) on the foot insert panel 172 of the foot insert 170, or alternatively, the massaging bumps 184 on the foot insert panel 182 of the foot insert 180, may massage the foot of the user as the user's foot remains in place on the foot insert 170 or foot insert 180, in the event that either one of these alternative foot inserts 170 and 180 are installed in lieu of foot insert 160. Once the user stops pressing the pump 148, elastic deformability of the pump 148 causes the pump 148 to deform upwards back to its original, undeformed position (FIG. 7), suctioning air into the reservoir interior 138 through the vent 146 in the cap 142.

After use, the foot insert 160 may be removed from the foot cavity 128 of each foot sanitizing unit 102. The foot insert 160 may be washed and replaced in the foot cavity 128, or set aside for storage. If needed, replacement sanitizing fluid 156 may be placed in the reservoir interior 138 of the fluid reservoir 136 preparatory to subsequent use of the foot sanitizing device 100. For this purpose, the user may unthread the cap 142 from the fluid reservoir 136 to gain access to the reservoir interior 138 and refill the reservoir interior 138 with replacement sanitizing fluid 156, and reconnect the cap 142 when finished refilling.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A foot sanitizing device, comprising:
    two foot sanitizing units, each foot sanitizing unit comprising:
        a base having a foot cavity formed on a top side of the base;
        a fluid reservoir provided on the base and comprising a reservoir interior, wherein the reservoir interior is in fluid communication with the foot cavity and is configured to contain a supply of fluid;
        a user-operable pump configured to pump fluid from the fluid reservoir into the foot cavity;
        at least one first fastener portion on one side of the base and at least one second fastener portion on an opposite side of the base, wherein each first fastener portion is configured to interlock with a corresponding one of the at least one second fastener portion; and
    a foot insert, removably attachable to the foot cavity to provide a contact interface for a user's foot to contact.

2. The foot sanitizing device of claim 1, wherein the base of each foot sanitizing unit is elongated along a longitudinal direction, and the foot cavity is elongated along said longitudinal direction.

3. The foot sanitizing device of claim 1, wherein each foot sanitizing unit further comprises a pair of base side walls extending upwardly from opposite transverse side edges of the base.

4. The foot sanitizing device of claim 1, wherein the base comprises at least one bottom suction cup extending downwardly from the base and configured to facilitate securement of the base on a hard floor or surface.

5. The foot sanitizing device of claim 1, wherein the base comprises at least one bottom spike extending downwardly from the base and configured to facilitate securement of the base on a carpet.

6. The foot sanitizing device of claim 1, wherein each foot sanitizing unit further comprises a pair of base side walls extending upwardly from opposite base side edges of the base, and further wherein the at least one first fastener portion is arranged on one of the pair of base side walls and the at least one second fastener portion is arranged on the other of the pair of base side walls.

7. The foot sanitizing device of claim 1, wherein the first fastener portion comprises an interlock flange and the second fastener portion comprises an interlock cavity configured to couple to the interlock flange.

8. The foot sanitizing device of claim 1, wherein the fluid reservoir is arranged at a proximal longitudinal end of the base and the foot cavity is arranged distally of the fluid reservoir and pump.

9. The foot sanitizing device of claim 1, wherein each foot sanitizing unit comprises a fluid conduit extending from the fluid reservoir to a fluid discharge opening formed in a floor of the foot cavity.

10. The foot sanitizing device of claim 9, wherein a fluid conduit space extends along the base and is configured to receive the fluid conduit.

11. The foot sanitizing device of claim 10, wherein the fluid conduit is received in the fluid conduit space such that the fluid conduit does not protrude outwardly from the fluid conduit space.

12. The foot sanitizing device of claim 1, wherein each foot insert comprises at least one fluid discharge opening through which the sanitizing fluid may be discharged towards a top side of the foot insert.

13. The foot sanitizing device of claim 1, wherein each foot insert comprises at least one of a rough texture, a plurality of bristles and a plurality of massaging bumps.

14. A foot sanitizing device, comprising:
at least one foot sanitizing unit comprising:
a base having a foot cavity formed on a top side of the base;
a fluid reservoir provided on the base and comprising a reservoir interior, wherein the reservoir interior is in fluid communication with the foot cavity and is configured to contain a supply of fluid;
a user-operable pump configured to pump fluid from the fluid reservoir into the foot cavity; and
a foot insert, removably attachable to the foot cavity to provide a contact interface for a user's foot to contact, wherein the foot insert comprises a foot insert panel configured to fit into the foot cavity and at least one insert locking clip configured to interlock with a companion clip opening in the base.

\* \* \* \* \*